(12) United States Patent
Massague et al.

(10) Patent No.: US 7,829,066 B2
(45) Date of Patent: Nov. 9, 2010

(54) ASSAY FOR ANTI-METASTATIC AGENTS

(75) Inventors: Joan Massague, New York, NY (US); Larry Norton, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 129 days.

(21) Appl. No.: 12/005,302

(22) Filed: Dec. 27, 2007

(65) Prior Publication Data

US 2008/0175791 A1 Jul. 24, 2008

Related U.S. Application Data (60) Provisional application No. 60/877,159, filed on Dec. 27, 2006.

(51) Int. Cl.
*A61K 49/00* (2006.01)
*C12Q 1/66* (2006.01)
*C12Q 1/68* (2006.01)

(52) U.S. Cl. .................. 424/9.6; 435/4; 435/6; 435/8

(58) Field of Classification Search .............. None
See application file for complete search history.

(56) References Cited

U.S. PATENT DOCUMENTS

2008/0213258 A1  9/2008  Massague et al.

FOREIGN PATENT DOCUMENTS

WO    WO 2006/074367 A3    7/2006

OTHER PUBLICATIONS

Drexler et al (Leukemia and Lymphoma, 1993, 9:1-25).*
Zellner et al (Clin. Can. Res., 1998, 4:1797-17802).*
Stein et al (Cancer Research, Apr. 2004, 64:2805-2816).*
Norton and Massague (Nature Medicine, Aug. 2006, 12:875-878, IDS).*
Hyoudou et al (Clinical Cancer Research, 2004, 10:7685-7691).*
Hart (American Journal of Pathology, 1979, 97:587-600).*
Minn, et al., "*Genes that mediate breast cancer metastasis to lung*", Nature, 436, 2005, pp. 518-524.
Norton et al., "*Is cancer a disease of self-seeding?*", Nature Medicine, 12(8), 2006, pp. 875-878.
Minn et al., "*Lung metastasis genes couple breast tumor size and metastatic spread*", PNAS, 104(16), 2007, pp. 6740-5745.
Kim, et al., "*Tumor Self-Seeding by Circulating Cancer Cells*", Cell 139, 2009, pp. 1315-1326 plus supplemental pages.
Leung et al., "*Tumor Self-Seeding: Bidirectional Flow of Tumor Cells*", Cell, 139, 2009, pp. 1226-1228.
Hujanen et al., "*Migration of Tumor Cells to Organ-derived Chemoattractants*", Cancer Research, 45, 1985, pp. 3517-3521.
Tanaka et al., "*Chemokines in tumor progression and metastasis*", Cancer Sci, 96(6), 2005, pp. 317-322.

\* cited by examiner

*Primary Examiner*—Laura B Goddard
(74) *Attorney, Agent, or Firm*—Venable LLP; Nancy J. Axelrod; Ann S. Hobbs (57) ABSTRACT

This invention relates, e.g., to a method for identifying an agent that inhibits a metastatic cell (e.g. that inhibits cancer metastasis), comprising measuring the amount of seeding of a tumor by a detectably labeled, metastatic cell, in a subject, in the presence and absence of a putative agent, wherein the amount of seeding by the metastatic cell is proportional to the metastatic potential of the cell, and wherein a significant amount of inhibition of the seeding by the putative agent indicates that the putative agent is effective to inhibit the metastatic cell (e, g, cancer metastasis). Also described are kits suitable for performing methods of the invention.

20 Claims, 4 Drawing Sheets

ASSAY FOR ANTI-METASTATIC AGENTS

This application claims the benefit of the filing date of U.S. provisional application 60/877,159, filed Dec. 27, 2006, which is incorporated by reference herein in its entirety.

FIELD OF THE INVENTION

This invention relates, e.g., to assays for identifying anti-metastatic agents, and kits for conducting the assays.

BACKGROUND INFORMATION

One of the greatest problems in the treatment of cancerous tumors is metastasis, i.e., the transmission of cells of a primary tumor to other locations in the patient and the establishment of new tumors at such locations. The spread of cancer cells from a primary tumor to a site of metastasis formation involves multiple interactions such as invasion of extracellular matrix, neovascularization, invasion of the blood vessel wall (intravasation), exit from the circulation (extravasation) and establishment of secondary growth. The complexity of the processes involved in metastasis has made it particularly difficult to develop effective treatments to inhibit or prevent the spread of metastatic cancer.

Moreover, metastasis is difficult to control because it often occurs before a primary tumor is diagnosed and treated and because the points of metastasis become multiple and therefore at some point impossible to treat by location-directed therapies such as radiation or surgery. Moreover, the metastatic lesions may be in locations which limit the possible dosages of the treatments, e.g., radiation, due to the sensitivity of the surrounding tissue to such treatments. Further, metastatic cells are heterogeneous, and cells which are resistant to conventional therapy tend to emerge.

Many current methods for identifying and validating anti-metastatic agents require that an investigator introduces a putatively therapeutic agent into a subject having a primary tumor and waits for metastatic tumors to arise, to determine if the agent inhibits metastases of the tumor. Waiting for a metastasis to develop is time-consuming, and the investigator cannot predict in advance where a metastasis will occur, and thus must monitor a variety of potential sites of metastasis. There remains a need to develop a rapid and efficient method to identify anti-metastatic agents and methods.

DESCRIPTION OF THE DRAWINGS

FIG. 1a shows transcriptomic microarray profiling performed on parental MDA-MB-231 cells, and in vivo selected lung metastatic LM2 subpopulation (LM2-4175, ref. 9), and cells derived from parental MDA-MB-231 mammary fat pad tumors. Mammary tumor denotes a sample from which in vivo mRNA expression was assessed directly from a fresh frozen primary tumor lysate, whereas passages A and B represent in vitro analyses of independent isolates of cells purified from dissociated MDA-MB-231 primary tumors. The heatmap corresponds to relative gene expression levels for 95 previously identified lung metastasis genes (113 probe sets), with red being high and blue indicating low expression. Gene labels are provided for gene clusters of interest due to partial selection during outgrowth of a parental MDA-MB-231 primary tumor. Genes highlighted in bold are functionally validated mediators of lung metastasis, or are included in the 18-gene LMS. FIG. 1b shows confirmation of microarray-based gene expression levels using quantitative RT-PCR analysis. Expression values for representative lung metastasis genes were normalized to parental MDA-MB-231 expression levels, and displayed graphically as a heatmap.

FIG. 2a shows parental or LM2 cells that were implanted into the mammary fat pad of immuno-compromised mice. Tumors were extracted at the indicated times, fixed and paraffin embedded sections stained with H and E. Images were captured under brightfield microscopy at 10×. T=tumor cells. N=areas of necrosis. FIG. 2b shows a schematic of experimental design. Parental cells expressing RFP were implanted into the mammary gland and allowed to grow. Animals bearing palpable tumors were then injected through the left ventricle with cells (parental or LM2) expressing GFP-firefly luciferase. FIG. 2c shows representative images of firefly luciferase bioluminescent measurements. Arrows indicate a growing signal originating from the pre-established mammary tumor. Luciferase luminescence occurred in 3 out of 3 mice injected with LM2 cells and in none out of 3 mice injected with parental cells. FIG. 2d shows tumors measured in FIG. 2c that were extracted from animals post-necropsy, fixed and frozen. Sections were scanned by automated microscopy and multiple fields assembled by montage. Stars denote areas of necrosis. FIG. 2e shows confocal microscopy of the same tumor at 20×and 63×. The inset depicts an area where the presence of nuclear-excluded GFP positive cells is confirmed. FIG. 2f shows mice bearing parental or LM2 tumors of various sizes that were sacrificed and bled via cardiac puncture. Mouse blood was lysed and plated in culture. Tumor cell colonies were scored and plotted as a function of tumor volume. FIG. 2g shows a schematic of a cross-seeding experiment. FIG. 2h shows RFP-expressing LM2 cells that were injected into one mammary fat pad while the contra-lateral mammary gland is implanted with GFP-labeled LM2 cells. A mouse implanted in only one mammary fat pad with RFP-expressing tumor cells was used to generate a control tumor. RFP labeled tumors were extracted after 58 days, fixed and frozen. Sections from control and seeded tumors were visualized under confocal microscopy at 20×.

DESCRIPTION OF THE INVENTION

The present inventors have found, surprisingly, that circulating metastatic cells are very effective at seeding tumor cells (e.g., the primary tumor from which they originated), and that the amount of this seeding is proportional to the metastatic capacity of the metastatic cells. This observation provides the basis for an assay for the identification of, and/or the validation of, agents that can inhibit metastatic cells. Putative agents are monitored for their ability, compared to a control, to inhibit the seeding of a metastatic cell to a tumor in a subject, or to inhibit the seeding, in vitro, of a metastatic cell to a colony of tumor cells (e.g., to a colony of cells from which the metastatic cell originated, or to a colony of different tumor or metastatic cells). An agent that can inhibit a metastatic cell, as used herein, includes an agent that can inhibit the seeding of a metastatic cell at a new site, at an established metastatic site, or into a primary tumor. Agents that inhibit the seeding of metastatic cells at new sites or at metastatic sites are sometimes referred to herein as agents that inhibit metastasis (anti-metastatic agents). Agents that inhibit the seeding of metastatic cells into a primary tumor in effect inhibit the growth of the tumor as a result of such seeding.

Metastatic cells that "seed" a tumor, as used herein, colonize the tumor and, in some circumstances, outgrow the resident tumor cells (dominate the tumor). In methods of the invention, the metastatic cells colonize the tumor in a manner such that the outgrowth of the metastatic cells is easily detectable (e.g. by means of a detectable label on the metastatic cells) and can thus be scored easily by an investigator.

Several embodiments of the method are described herein. For example, in one embodiment, an investigator introduces a cell from a tumor or tumorigenic cell line (a tumorigenic cell) into a suitable site of an immuno-compromised subject, such as a SCID mouse, and allows the cell to form a tumor; introduces a detectably labeled metastatic cell (e.g. a metastatic cell derived from the tumorigenic cell or from a different source) into the subject; and measures the amount of seeding of the tumor by the metastatic cell, in the presence and absence of an agent of interest (e.g., a candidate for an anti-metastatic agent, or a putative anti-metastatic agent). In another embodiment, an investigator allows a tumor to form in a cancer prone subject, introduces a detectably labeled metastatic cell into the subject, and measures the amount of seeding of the tumor by the metastatic cell, in the presence and absence of the agent. In another embodiment, an investigator introduces a detectably labeled cell from a metastatic cell line into a first suitable site of an immuno-compromised subject, such as a SCID mouse; introduces a second cell from the metastatic cell line or a cell from a different metastatic cell line into a second suitable site of the subject; allows the first and second cells to form tumors; and measures, in the presence and absence of the putative agent, the amount of seeding of the tumor at the second site by labeled cells shed from the tumor at the first site. In another embodiment, an investigator allows colonies to form from a tumor or metastatic cell, in a suitable medium in vitro; contacts the colonies with a detectably labeled metastatic cell; and measures the amount of seeding of the colony by the metastatic cell, in the presence and absence of the agent. The seeding may be measured as a function of time (e.g. after a preset time has elapsed).

As used herein, the singular forms "a," "an," and "the" include plural referents unless the context clearly dictates otherwise. For example, "an" agent, as used above, encompasses one or more agents; and "a" detectably labeled metastatic cell encompasses one or more such cells, which can be the same or different.

A method of the invention can be used to screen for new anti-metastatic agents, or to evaluate and/or characterize candidates for anti-metastatic agents. Agents identified by a method of the invention can be used, e.g., for the prevention or for the treatment of cancer metastasis and/or for the inhibition of growth of primary tumors caused by the seeding of the tumors with metastasized cells from the same or from a different tumor.

Advantages of a method of the invention include that it can be performed rapidly, without having to wait for a metastasis to occur in the subject; and it is efficient, in that an investigator can readily monitor seeding of a tumor at a known site. In embodiments using in vitro methods, advantages include that the assay can be conducted without the need for a subject, and that the assay can be conducted economically (e.g., using multi-well plates that require minimal use of the agent to be tested and inexpensive cell culture methods and materials). Such in vitro methods can be readily adapted to high throughput methods, e.g. using robotic or other automated procedures. Furthermore, by selecting a variety of pairs of a suitable tumor (e.g. having a defined degree of metastatic potential) and a suitable metastatic cell (e.g. exhibiting a defined degree of metastatic potential, or a preference for a specific site of metastasis), the method can be used to identify a variety of anti-metastatic agents, which affect different stages of metastasis, and/or which are directed against metastases to particular tissues.

One aspect of the invention is a method for identifying an agent that inhibits a metastatic cell, comprising measuring the amount of seeding of a tumor by a detectably labeled metastatic cell in a subject, in the presence and absence of a putative agent; wherein the amount of seeding by the metastatic cell is proportional to (a function of) the metastatic potential (ability, activity, capacity) of the cell; and wherein a significant amount of inhibition of the seeding by the putative agent indicates that the putative agent is effective to inhibit cancer metastasis. The amount of seeding by the metastatic cell may be determined by measuring the amount of the detectable marker (e.g., a fluorescent marker or luciferase) at the site of the tumor.

Another aspect of the invention is a method that comprises: (a) introducing a cell from a tumorigenic cell line or tumor (a tumorigenic cell) into a suitable site of an immuno-compromised subject (e.g. a SCID mouse) and allowing the cell to form (grow to) a tumor; (b) introducing into the subject, by a systemic route, a detectably labeled metastatic cell, e.g. from a cell line that has been derived from the tumor, from another tumor, or from a tumorigenic cell line (e.g. by injecting the cell into the arterial circulation, as by injection into the heart); and (c) measuring the amount of seeding of the tumor by the metastatic cell in the presence and absence of a putative anti-metastatic agent. In this, and in other, methods of the invention, a significant amount of inhibition of the seeding by the putative agent indicates that the putative agent is effective to inhibit cancer metastasis.

In one embodiment of this method, the tumorigenic cell is from a breast tumor or a tumorigenic cell line derived from a breast tumor (e.g., an MDA-MB-231 cell); and the metastatic cell is a derivative of the tumorigenic cell, which metastasizes preferentially to lung, bone or brain (e.g., an LM2 cell, which is a metastatic derivative of the MDA-MB-231 cell line that metastasizes preferentially to lung).

Another aspect the invention is a method that comprises: (a) allowing a tumor to form in a subject that is cancer prone (e.g., susceptible to developing tumors); (b) introducing into the subject, by a systemic route, a detectably labeled metastatic cell (e.g. injecting the cell into the arterial circulation, as by injection into the heart); and (c) measuring the amount of seeding of the tumor by the metastatic cell in the presence and absence of a putative anti-metastatic agent. Subjects that are cancer-prone are well-known and include, e.g., a transgenic mouse that overexpresses one or more oncogenes; a mouse defective in one or more tumor suppressor genes, e.g. comprising knockouts for one or more tumor suppressor genes; etc. Suitable oncogenes or tumor suppressor genes will be evident to the skilled worker. Suitable tumor suppressor genes include, e.g., p53, p16, RB, etc. For these and other examples of cancer prone subjects, see also the world wide web site mouse.ncifcrf.gov/available_strains.asp.

Another aspect of the invention is a method that comprises: (a) introducing a first detectably labeled cell from a metastatic cell line into a first suitable site of an immuno-compromised subject (e.g. a SCID mouse); (b) introducing a second cell from the metastatic cell line (or a metastatic cell from a different source) into a second suitable site of the subject; (c) allowing the first and second cells to form tumors; and measuring, in the presence and absence of a putative metastatic agent, the amount of seeding of the tumor at the second site by labeled cells shed from the tumor at the first site. If desired, the second cell from the metastatic cell line may be labeled with a second detectable label, and the amount of labeled cells shed from the tumor at the second site and seeded at the tumor at the first site may also be measured, in the presence or absence of the putative agent.

Another aspect of the invention is a method that comprises: (a) allowing tumorigenic (including metastatic) cells to form colonies in a first layer of soft agar; (b) overlaying the first soft agar layer with a second layer of soft agar comprising detectably labeled metastatic cells; and (c) measuring the amount of seeding of a colony in the first layer by metastatic cells, in the presence and absence of a putative anti-metastatic agent.

In a method of the invention, the metastatic cell line may obtained by serially passaging metastasized cells from a tumor or tumorigenic cell line through immuno-compromised animals (e.g. for at least one or at least two cycles), to obtain, in each round of passage, cells that are more metastatic than the cells from the previous round of passage. A metastatic cell used in a method of the invention may significantly up-regulate or down-regulate a plurality of the genes listed in Table 1 (e.g. at least about 10 or 15 of the genes, or as many as all 18 of the genes). For example, two or more of the following genes from Table 1 may be up-regulated: MMP1, CXCL1, PTGS2/COX2, VCAM1, ID1, epiregulin, MMP2, SPARC, IL13R2, TNC, FSCN1, ANGPTL4, CXCL1, and/or FSC1. In embodiments of the invention, the following combinations of genes may be upregulated: epiregulin in combination with one or more of MMP1, MMP2 or PTGS2; MMP1, MMP2 and PTGS2; one or more of TNC, FSCN1, ANGPTL4 or CXCL1; TNC and FSC1; TNC and ANGPTL4; or ANGPTL4 and KRTHB1.

In another embodiment of this method, the metastatic cell used in the method is generated by transfecting a suitable host cell (e.g. a tumorigenic cell), with one or more (e.g., 2 or more, 3 or more, 4 or more) of the up-regulated genes listed in Table 1. The transfected genes may be, e.g., any of the combinations of genes noted above.

A method of the invention may be used for identifying (e.g., screening for or validating) an agent that inhibits (e.g. prevents) metastasis of a tumor of interest; or it may be a method for identifying (e.g., screening for or validating) an agent for treating a subject having a tumor of interest; or it may be a method for identifying (e.g., screening for or validating) an agent for treating a subject having metastasis.

Another aspect of the invention is a kit for identifying an agent that inhibits a metastatic cell, comprising a cell from a tumorigenic cell line (e.g. a cell from a breast cancer derived tumor line, such as MDA-MB-231); and cells from one or more metastatic cell lines derived from the tumorigenic cell (e.g. cells that preferentially metastasize to lung, brain or bone, including cells from the LM2 cell line, which metastasizes preferentially to lung). Optionally, the kit may also contain one or more containers to hold the cells.

This invention relates, e.g., to a method for identifying an agent that inhibits a metastatic cell. As used herein, the term "an agent that inhibits a metastatic cell" includes an agent that inhibits a metastatic cell in a subject, or an agent that is a candidate for further testing. Such inhibitory agents include, e.g., agents that inhibit the metastasis of a cell from a primary tumor, or the further metastasis of a cell from a site of metastasis. Furthermore, the inventors show herein that metastatic cells can sometimes re-seed a primary tumor from which they have arisen, thereby increasing the size (growth) of the primary tumor. Therefore, an inhibitory agent identified by a method of the invention may inhibit such growth of a primary tumor. As noted, the present inventors have found that circulating metastatic cells are very effective at seeding tumor cells (e.g., the primary tumor from which they originated), and that the amount of this seeding is proportional to the metastatic capacity of the metastatic cells. Without wishing to be bound by any particular mechanism, it is suggested that the properties which contribute to metastatic behavior also contribute to such re-seeding behavior, and that agents which inhibit such re-seeding can also inhibit metastatic behavior.

As used herein, "metastasis" refers to the ability of cells of a cancer (e.g. a primary tumor, or a metastasis tumor) to be transmitted to other locations in the subject and to establish new tumors at such locations. An agent that "inhibits" cancer metastasis may function at any of a variety of steps in metastatic progression. For example, it may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell.

In methods of the invention, the amount of seeding of a tumor (e.g. a resident tumor) by a metastatic cell is measured. A "metastatic" cell, as used herein, refers to a cell that has a potential for metastasis and, when used in a method of the invention, is able to seed a tumor or a cell colony of interest. A "highly metastatic" cell, as used herein, refers to a cell that has a high potential for metastasis; cells from the cell line, LM2, described herein, can be considered to be highly metastatic cells. Metastatic cells can be generated in a variety of ways, which are discussed further below.

A "tumorigenic cell," as used herein, is a cell that, when introduced into a suitable site in a subject, can form a tumor. The cell may be non-metastatic or metastatic. A variety of types of tumorigenic and/or metastatic cells can be used in a method of the invention, including cells from metastatic epithelial cancers, carcinomas, melanoma, leukemia, etc. The tumor cells may be, e.g., from cancers of breast, lung, colon, bladder, prostate, liver, gastrointestinal tract, endometrium, tracheal-bronchial tract, pancreas, liver, uterus, ovary, nasopharynges, prostate, bone or bone marrow, brain, skin or other suitable tissues or organs. In a preferred embodiment, the cancer cells are of human origin.

Generally, in selecting a tumorigenic cell to use in a method of the invention, it is desirable to select a cell that can form a tumor when introduced into a comparable site from which the tumor originated, but in another animal (an orthotopic site, e.g. a tumor from a human breast cancer introduced in the mammary fat pad of a mouse), or that can form a tumor when introduced into a different site (an ectopic site) in a suitable subject. A "suitable site" for the introduction of a tumorigenic cell, as used herein, is a site at which such a cell can grow to form a tumor that can subsequently be monitored for seeding by a circulating metastatic cell. The introduction (placement, transplantation) of a tumorigenic cell into the same type of tissue of origin (an orthotopic site) or into a different site (an ectopic site) allows for ready access to the resulting tumor for the detection and analysis of seeding by metastatic cells. For example, a cell from a mammary (breast)

tumor can be readily implanted into a mammary fat pad, a prostate tumor cell into a prostate gland, or a skin cancer cell, such as a melanoma, subcutaneously.

Suitable tumorigenic cells will be evident to the skilled worker. These include, for example, HeLa cells, carcinoma and sarcoma cell lines, well established cell lines such as the human lung adenocarcinoma line Anip 973, as well as human breast cancer lines MDA-MB-231, MDA-MB-468 and MDA-MB-435, human prostate cancer lines PC3 and DU-145, human glioblastoma line 324, mouse melanoma B16, and others that have been reported or may become available in the art, including, immortalized cells prepared in the laboratory.

Suitable procedures for growing the initial (resident) tumor are conventional, and generally involve transcutaneous injection or implantation through an incision of the tumor cells into the subject. The Examples herein illustrate typical methods for introducing such cells into a subject. After administration, solid tumors generally develop, typically at the site of the injection. Generally, a tumor is allowed to grow until it is of a suitable size such that, when labeled metastatic cells are introduced and seed the tumor, the seeded tumor can be detected. For example, the tumor can reach a sufficient size such that metastatic cells labeled with a luciferase marker can seed the tumor in sufficient amounts to be detected at the site of the tumor by an in vivo bioluminescence imaging system. In some embodiments of the invention, the tumors are palpable when the metastatic cells are introduced into the subject.

Any suitable subject may be used, provided a tumor can be grown in the subject. Suitable subjects include a variety of vertebrates, including mammals, e.g. convenient laboratory animals such as rabbits, rats, mice, and the like. For closer analogy to human subjects, primates can also be used. Particularly useful are subjects that are particularly susceptible to tumor development, such as subjects with impaired immune systems, typically nude mice or SCID mice. Any appropriate subject can be used, the choice being dictated mainly by convenience and similarity to the system of ultimate interest.

In an embodiment in which the method is carried out in vitro, any suitable system can be used. Suitable in vitro systems will be evident to the skilled worker. For example, one such system is a modified soft agar assay in which at least two cell layers are poured. A first layer contains tumorigenic or metastatic cells that are detectably labeled with a first label, and that are allowed to grow until they form colonies, A second layer, containing metastatic cells labeled with a second detectable label, is then poured over the first layer. In the presence or absence or one of more putative anti-metastatic agents, the cells in the two layers are allowed to migrate in or out of each layer. Colonies containing cells with the two labels are identified after a suitable length of time, using an appropriate microscope and/or label-analyzing method. In another embodiment, only the metastatic cells in the second layer, or only the cells in the first layer, are detectably labeled. A typical in vitro method is illustrated in Example III.

A variety of metastatic cells, derived from a variety of sources, can be used in a method of the invention. Several methods are available for isolating such metastatic cells. For example, one can perform serial passages of potentially metastatic cells, or of heterogenous populations of cells that contain metastatic cells, through immuno-compromised hosts, in order to derive or select cells with increased metastatic potential. The cell which is passaged is preferably a tumorigenic cell, and may be serially passaged in this manner for one or more cycles (e.g. for two, three or more cycles). Any of a variety of tumorigenic cells, at any stage of metastasis, can be used to derive metastatic cells in this manner. For example, one can begin with a cell or cell line taken from an early stage primary tumor, or from a more advanced tumor, or from a tumor that has metastasized to, e.g., a lymph node, lung, bone, brain, liver, chest wall, pleural cavity, pleural fluid, intestines, skin, ovary or other tissue or organ. Alternatively, metastatic cells can be obtained directly from metastatic lesions by known methods for creating cell cultures out of biopsies.

The Examples herein illustrate the use of a tumorigenic cell line—MDA-MB-231 (sometimes referred to herein as "MDA-231")—as the starting cell line. This cell line was derived from a pleural effusion of a human breast cancer. In experiments from the inventors' laboratory, which are described in Minn et al. (2005) Nature 436, 518-24 and WO/2006/074367, cells from this cell line were injected into a mammary fat pad of a SCID mouse, and metastases were allowed to appear in the lung. Metastasized cells were isolated from the lung, amplified, and injected into a mammary fat pad of another SCID mouse, and the metastasized cells were again collected from the lung and amplified. After the two rounds of selection, a sub-population of metastatic cells, which metastasized preferentially to the lung, was obtained. The resulting cell line is called LM2.

In the publications noted above, the inventors identified and characterized genes whose expression is modified (up-regulated or down-regulated) in LM2 cells. About 54 genes were reported to exhibit modified levels of expression in lung metastatic cells. Table 1 below shows 18 of those genes whose expression level is significantly correlated with lung metastasis, as indicated by the p values. These 18 genes constitute a "lung metastatic signature (LMS)."

TABLE 1

| p-value | UG cluster | Gene symbol | Description | |
|---|---|---|---|---|
| <0.000001 | Hs.118400 | FSCN1 | Fascin homolog 1, actin-bundling protein (*Strongylocentrotus purpuratus*) | + |
| <0.000001 | Hs.83169 | MMP1 | Matrix metalloproteinase 1 (interstitial collagenase) | + |
| <0.000001 | Hs.9613 | ANGPTL4 | Angiopoietin-like 4 | + |
| 0.000006 | Hs.74120 | C10orf116 | Chromosome 10 open reading frame 116 | + |
| 0.00002 | Hs.789 | CXCL1 | Chemokine (C-X-C motif) ligand 1 (melanoma growth stimulating activity, alpha) | + |
| 0.000355 | Hs.196384 | PTGS2 | Prostaglandin-endoperoxide synthase 2 (prostaglandin G/H synthase and cyclooxygenase) | + |
| 0.000444 | Hs.185568 | KRTHB1 | Keratin, hair, basic, 1 | + |
| 0.000506 | Hs.109225 | VCAM1 | Vascular cell adhesion molecule 1 | + |
| 0.000627 | Hs.17466 | RARRES3 | Retinoic acid receptor responder (tazarotene induced) 3 | − |

TABLE 1-continued

| p-value | UG cluster | Gene symbol | Description | |
|---|---|---|---|---|
| 0.001263 | Hs.368256 | LTBP1 | Latent transforming growth factor beta binding protein 1 | + |
| 0.004365 | Hs.444471 | KYNU | Kynureninase (L-kynurenine hydrolase) | + |
| 0.005179 | Hs.421986 | CXCR4 | Chemokine (C-X-C motif) receptor 4 | − |
| 0.006426 | Hs.77667 | LY6E | Lymphocyte antigen 6 complex, locus E | − |
| 0.007153 | Hs.410900 | ID1 | Inhibitor of DNA binding 1, dominant negative helix-loop-helix protein | + |
| 0.010871 | Hs.255149 | MAN1A1 | Mannosidase, alpha, class 1A, member 1 | + |
| 0.032361 | Hs.388589 | NEDD9 | Neural precursor cell expressed, developmentally down-regulated 9 | − |
| 0.03713 | Hs.115263 | EREG | Epiregulin | + |
| 0.046859 | Hs.98998 | TNC | Tenascin C (hexabrachion) | + |

Of these 18 genes, the 14 genes noted with plus signs are up-regulated.

As functional validation of genes that are involved in lung metastasis, the authors reported that at least six of the genes from Table 1: MMP1, CXCL1, PTGS2/COX2, VCAM1, ID1 and epiregulin, as well as three additional genes: MMP2, SPARC and IL13R2, can convert a non-metastatic host into a metastatic one if they are stably transfected into the host cell, in various suitable combinations. Furthermore, in subsequent short hairpin RNAi knockout studies, the inventors reported that a 2-fold reduction of ID1, VCAM1 or IL13R2 decreased lung metastatic activity of LM2 cells by more than 10-fold; and that if various combinations of the four genes—MMP1, PTGS2, epiregulin and MMP2—are knocked out in LM2 cells, the cells exhibit a reduced ability to be metastatic. For example, although knockouts of individual genes do not render a cell non-metastatic, knockouts of combinations of epiregulin and one of the other three genes, or a combination of MMP1, MMP2 and PTGS2, will render the cell non-metastatic.

Further studies by the inventors have now validated about 4-5 additional genes that are involved in lung metastasis. For example, lung metastasis by LM2 cells is decreased by RNAi-mediated knockdown of Tenascin C (TNC), Fascin 1 (FSCN1) Angiopoietin-like 4 (ANGPTL4) or CXCL1 individually, or by the combined knockdown of TNC and FSC1, TNC and ANGPTL4, ANGTL4 and Keratin 81 (KRT81, also known as Keratin hair basic-1 KRTHB1), A metastatic cell that can be used in a method of the invention can be a cell wherein a plurality (e.g. at least about 2, 5, 10, 15, 30, 40 or more of the 54 genes whose expression was shown to be correlated with metastasis) are significantly up-regulated or down-regulated, or wherein a plurality (e.g. at least about 2, 5, 10, 15 or more, or all 18) of the 18 genes listed in Table 1 are significantly up-regulated or down-regulated. By "significantly up- or down-regulated" is meant herein that the level of mRNA or protein encoded by this gene is increased or decreased by at least two-fold with a p value >0.05.

Another method for generating a metastatic cell to be used in a method of the invention is to stably transfect suitable genes whose expression is correlated with metastasis into a suitable host cell, preferably a tumorigenic cell. Any of the cell types discussed herein as starting cells for the in vivo selection of metastatic cells can be used.

Suitable combinations of genes selected from the 54 genes whose expression is shown to be correlated to lung metastasis, as well as other correlated genes, can be used. In a preferred embodiment, the genes are selected from the 14 up-regulated genes of Table I. For example, one can transfect one or a plurality (e.g. 3 or 4) of the genes into a suitable host cell. Other suitable genes are genes that have been reported to constitute a bone metastasis signature. See, e.g., Kang et al. (2003) Cancer Cell 3, 537-49

Criteria for selecting genes to be transfected include: the gene should be functionally validated, e.g. by a knock out experiment as above; and the gene should be clinically validated. That is, the gene should be shown to be over-expressed in metastasized tumors from patients in the clinic, and/or they should be shown to be over-expressed in biopsies or other post-mortem tissue.

The number of genes which must be transfected into a cell to render it metastatic is a function of, e.g., the metastatic capacity of the cell, the degree of metastasis conferred by the gene(s), and/or the desired metastatic potential of the metastatic cell to be generated. For example, a cell which already exhibits an intermediate metastatic potential can be transfected with only one or two genes from a metastatic signature to convert it to a metastatic cell. By contrast, a cell which is indolent for metastasis may require transfection by a greater number of genes in order to render it metastatic. Current technology allows for the co-transfection of up to four genes. However, the method of transfecting cells to generate metastatic cells encompasses introducing greater numbers of genes, as methods for performing multiple transfections become available.

Minn et al. (2005) (supra) and WO2006074367 provide methods for generating metastatic cells for lung, by transfecting MDA-231 cells with selected genes from the LMS profile shown in Table 1. Also, Kang et al. (2003) Cancer Cell 3, 537-49, a paper authored by some of the present inventors, describes the generation of metastatic cells that are bone-specific, by transfecting suitable cells with selected genes from a bone metastasis signature. Variations of these methods will be evident to the skilled worker.

The invention also includes a suitable combination of genes that can be used to render a cell metastatic. The genes can be operably linked to expression control signals, in expression vectors, and/or in any form that is suitable for transfecting host cells. Any of the genes noted above, or others, can be present in such a combination. The combination of genes can be in a composition that also includes a suitable tumorigenic cell, e.g. a composition that forms when the combination of genes is used to stably transfect the cell to generate a metastatic cell. The combination of genes can also be packaged in the form of a kit, e.g. for use in transfecting cells in order to render them metastatic.

Methods for cloning genes of interest under the control of suitable expression control sequences (e.g., promoters or other regulatory elements), in suitable vectors, and transfecting them stably into suitable cells are conventional. See, e.g., Sambrook et al., Molecular Cloning: A Laboratory Manual, Second Edition, Cold Spring Harbor, N.Y., (1989); Wu et al, *Methods in Gene Biotechnology* (CRC Press, New York, N.Y., 1997), *Recombinant Gene Expression Protocols, in Methods in Molecular Biology*, Vol. 62, (Tuan, ed., Humana Press, Totowa, N.J., 1997); and *Current Protocols in Molecular Biology*, (Ausabel et al, Eds.,), John Wiley & Sons, NY (1994-1999).

Briefly, a gene of interest is cloned to be operably linked to an expression control sequence. The term "expression control sequence," as used herein, refers to a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc. An expression control sequence is "operably linked" to a nucleotide coding sequence when the expression control sequence is positioned in such a manner to effect or achieve expression of the coding sequence. For example, when a promoter is operably linked 5' to a coding sequence, expression of the coding sequence is driven by the promoter. Suitable expression control sequences that can function in tumor cells will be evident to the skilled worker. For example, a promoter can be constitutive or regulatable (e.g. inducible), and it can be tissue- or organ-specific promoter.

Any suitable transfection method may be used to introduce a nucleic acid into a cell, including liposomes (e.g., lipofection), calcium phosphate precipitation, electroporation and use of a gene gun. Methods for selecting and characterizing stably transfected cells are conventional, as are methods of propagating the cells and storing them.

Another embodiment of the invention is an isolated metastatic cell, or progeny thereof, obtained by either the serial passage procedure or the transfection procedure as described above. Such a cell can be, e.g., part of a kit of the invention.

A variety of combinations of tumors and metastatic cells can be used in a method of the invention, provided that the metastatic cell can seed the tumor. In principle, any suitable pair of cells can be used.

In one embodiment of the invention, the metastatic cell is derived from the primary tumor whose seeding is measured in the assay. In this embodiment, the metastatic cell preferentially re-invades the parental tumor from which it was derived. The parental cell used to derive a metastatic cell can be a metastatically indolent cell, or one that is already somewhat metastatic, such as the cells in the pleural effusion used to derive LM2 cells. In another embodiment, the metastatic cell is paired in the assay with a tumor that is related to, but not identical with, the cells from which it was derived. For example, LM2 metastatic cells can be paired with a tumor generated from a breast cancer cell line other than MDA-MB-231. In another embodiment, the metastatic cell is paired with an unrelated tumor, e.g. a tumor from a different tissue or organ. Much of the present application is directed to methods in which a metastatic cell seeds a tumor. However, in other embodiments, a metastatic cell can colonize a wound, site of inflammation, stressed tissue, etc. whose cells express chemokines, cytokines, etc. that attract the metastatic cells.

Metastatic cells of the invention can be introduced into a subject by any of a variety of conventional methods. For example, the cells can be introduced systemically, e.g. by injection into a ventricle of the heart, which allows the cells to circulate in the arterial system. In another embodiment, the cells are introduced into the subject by tail vein injection. Cells introduced via tail vein injection travel into the lung capillaries, where they become trapped. This mode of introduction is particularly useful for introducing metastatic cells into lung tissue, e.g., for seeding metastatic cells to resident tumors that are in the lung. Another suitable means for introducing metastatic cells into a subject is to implant them orthotopically or ectopically into a suitable site. The Examples herein illustrate a method by which a breast tumor cell is introduced into two contralateral sites in a subject and allowed to grow into tumors at those sites. Cells are shed from one of the sites of tumor growth and migrate to, and seed, the tumor in the contralateral site.

A metastatic cell may be introduced into the subject before, or at the same time as, a tumorigenic cell (which can grow to form a tumor) is introduced. Preferably, however, the metastatic cell is not introduced until several days (e.g. about 3 days) after the tumorigenic cell has been introduced. This time lag provides adequate time for the implanted tumorigenic cell to "settle" and allows the subject to recover from the local trauma at the site of introduction (e.g. injection). In one embodiment, the metastatic cell is introduced into the subject after the tumor has become palpable.

In methods of the invention, the amount of seeding by the metastatic cells is measured in the presence or absence of a putative anti-metastatic agent. The "absence" of a putative metastatic agent means that the agent is not administered to the subject. A variety of suitable controls, in which the putative agent is absent, will be evident to the skilled worker. For example, a solution can be administered which is identical to the solution containing the putative agent (e.g. contains suitable buffers, stabilizers, etc), except that it lacks the putative anti-metastatic agent. In some embodiments, a series of different concentrations of the putative anti-metastatic agent can be administered, for example in order to quantitate the potency of the agent.

A variety of putative anti-metastatic agents can be tested in a method of the invention. For example, for particular polypeptide targets that have been identified, the agent can be an antibody or active antibody fragment against that target; or it can be an antisense nucleic acid which specifically targets expression of a target gene of interest; or it can be an interference nucleic acid (such as a small interference siRNA, or a short-hairpin shRNA) which specifically targets expression of a target gene of interest; or it can be a micro-RNA which specifically targets expression of a target gene of interest; or it can be protein or peptide anti-metastatic agent or a polynucleotide that expresses the polypeptide.

A variety of small molecules can also be tested for their ability to act as anti-metastatic agents. Naturally occurring or synthetic (man-made) small molecules can be used. Suitable small molecules, sometimes referred to herein as "compounds," can be isolated from natural sources or developed synthetically, e.g., by combinatorial chemistry. In general, such molecules are identified from large libraries of natural products or synthetic (or semi-synthetic) extracts or chemical libraries according to methods known in the art. Those skilled in the field of drug discovery and development, for example, will understand that the precise source of test extracts or compounds is not critical to the methods of the invention. Accordingly, virtually any number of chemical extracts or compounds can be used in the methods described herein.

Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, e.g., Biotics (Sussex, UK), Xenova (Slough, UK), Harbor Branch Oceanographics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

The invention includes agents identified, or confirmed to be active, by a method of the invention.

In methods of the invention to test putative agents, the agents can be administered to the subject by any of a variety of conventional methods. For example, a putative agent can be added systemically, intraperitoneally, orally, by inhalation, or it can be contacted directly with the tumor.

A putative agent can be introduced into a subject at any suitable time during a method of the invention. For example, the agent can be introduced before the metastatic cell has been introduced (e.g., to identify an agent that prevents metastasis), or together with or after the introduction of the metastatic cell (e.g., to identify an agent for use in the treatment of an existing metastasis, to prevent further metastases.)

Any of a variety of conventional labels can be used to label a metastatic cell to be used in a method of the invention. For example, suitable labels include green fluorescent protein (GFP), red fluorescent protein (RFP), and luciferase, whose use is described in the Examples. Other conventional labels include DsRed, EYFP, ECFP, EVFP and derivatives of EGFP. See also the markers listed at the web site of BD Biosciences (Clontech). When it is desirable to label two different cell populations at the same time (e.g., metastatic cells and cells of a resident tumor, or metastatic cells inoculated at two different (e.g. orthotopic and/or ectopic) sites in a subject), labels which can be easily distinguished can be used. For example, a first cell type can be labeled with a GFP and a second cell type with RPF; or a first cell type can be labeled with firefly luciferase and a second cell type with Renilla luciferase.

Methods for labeling cells are conventional. One such method, in which a retrovirus expressing a detectable polypeptide marker, such as a luciferase protein, is introduced into a cell to be labeled, is described in the Examples herein. Other methods include the use of a plasmid vector expressing a detectable polypeptide marker, or labeling of the cells by uptake of a vital dye.

Methods of detecting (e.g., quantitating) detectably labeled metastatic cells at the site of a resident tumor will be evident to the skilled worker. For example, when a metastatic cell is labeled with a fluorescent marker, it can be detected by examining, with a fluorescent microscope, a tissue sample from the tumor of the subject. When a metastatic cell is labeled with luciferase, the tumor can be examined in the living subject (e.g. in real time) by measuring light emission (bioluminescence) from the marker.

Methods of detection can be readily quantified by non-invasive photon flux emission measurement of luminesce (luciferase), non-invasive imaging of fluorescence, ex-vivo imaging of luminescence, ex-vivo imaging of fluorescence, fluorescence-activated sorting of tumor cells after dissociation of the extracted tumors into a cell suspension, immunohistochemical analysis of marker proteins, to provide quatitative, reproducible assays.

Agents are selected that significantly inhibit seeding by a metastatic cell of a resident tumor. By "significant" inhibition is meant that the agent inhibits the seeding by at least 2-fold to >1.000-fold more than does a control agent, with a p value >0.05.

Any combination of the materials useful in the disclosed methods can be packaged together as a kit for performing any of the disclosed methods. In particular, sets of tumorigenic and metastatic cells designed for use in an assay of the invention can be packaged together in a kit. For example, a kit can contain tumorigenic cells which, when allowed to form tumors, grow to tumors exhibiting a range of metastatic potentials. In another embodiment, a cell from a tumorigenic cell line may be packaged with a metastatic cell that has been derived from the tumorigenic cell, or with one or more unrelated metastatic cells. The metastatic cells can be, e.g., from one or more independent lines derived from metastases to the same tissue (e.g., lung), or from one or more independent cell lines from metastases to different tissues (e.g., lung, bone and/or brain). The inventors have isolated metastatic derivatives of the breast cancer cell line, MDA-MB-231, that preferentially metastasize to lung (LM2), bone (1833, 2287) and brain (Br-BnM2; H2030-BrainM2).

In one embodiment, a kit of the invention contains MDA-MB-231 cells and one or more metastatic derivatives of that cell line. In another embodiment, wherein a tumorigenic cell line is readily available to investigators, the kit contains one or more metastatic derivatives of the tumorigenic cell line, but not the tumorigenic cell line, itself.

In other embodiments, metastatic derivatives of a tumorigenic cell that exhibit a range of metastatic potentials, or that are defective in different steps of the metastatic process, can be packaged in a kit. With such a kit, an investigator can characterize the properties of a putative agent of interest. For example, if the metastatic cells represent a range of metastatic potential, one can determine the degree of metastatic potential at which a putative agent is effective. If the metastatic cells represent different stages of the metastatic process, one can isolate and/or characterize agents that act on particular steps of the metastatic process.

Cells in a kit can be packaged in small amounts, so that an investigator can use this starting material to generate cells for use in a method of the invention. In another embodiment, cells are packaged in amounts that are suitable for use in individual assays, or packaged in amounts from which suitable aliquots may be used in individual assays. Methods for packaging cells (e.g., frozen in the presence of a stabilizing component, such as glycerol or DMSO; in tissue culture vessels, such as flasks, etc) will be evident to the skilled worker. Suitable methods of packaging cells in kits will be evident to the skilled worker. For example, the cells can be packaged in a suitable medium in 1.8 ml. tubes that are resistant to freezing at −80° C. Cells in a kit of the invention may be labeled or unlabeled.

Optionally, kits of the invention may comprise instructions for performing the method. Other optional elements of a kit of the invention include suitable media components, reagents for labeling the cells (e.g., suitable retroviruses encoding a detectable label), packaging materials, etc. Reaction components for detecting the label can be included.

In the foregoing and in the following examples, all temperatures are set forth in uncorrected degrees Celsius; and, unless otherwise indicated, all parts and percentages are by weight.

EXAMPLES

Example I

Materials and Methods

Tumor gene expression profiles. Methods for RNA extraction, labeling, and hybridization for DNA microarray analysis of human primary breast tumors have previously been described for the MSK-99 and NKI-295 cohorts[9, 12]. The Erasmus-345 cohort consists of 286 published breast cancer samples[11, 13] that were curated and analyzed as described previously[11, 13] as well as an additional 59 samples (data unpublished). The MSK and Erasmus cohorts were analyzed using HG-U133A oligonucleotide microarrays (Affymetrix). The NKI samples were competitively hybridized against pooled reference cRNA to 25,000 element oligonucleotide microarrays[11, 13]. All relevant clinical information for patients included in the cohorts has previously been published[9, 11, 13, 22, 24], or is being provided as supplementary information.

Data analysis. Tumors from each cohort (MSK, Erasmus, NKI) were classified as LMS positive or negative based on a nearest centroid classifier as previously described[12]. Hierarchical clustering of normalized data with median centering of gene expression values was done using the 18 most univariately significant genes of the LMS[12] using TIGR MultiExperiment Viewer 3.1[25]. Kaplan-Meier survival analysis and Cox proportional hazards regression modeling was performed using the "survival" package 2.18 in the R statistical package 2.1.2 (world wide web site r-project.org). Significance Analysis of Microarrays (SAM) was done using the "samr" 1.20 package.

Cell lines. The parental MDA-MB-231 cell line was purchased from the American Type Tissue Collection (ATCC). LM2 cells are in vivo selected derivatives exhibiting aggressive lung metastatic activity, and have been previously described. Cells were cultured in DMEM supplemented with 10% fetal bovine serum.

RNA expression analysis. Total RNA was purified using the RNeasy kit (Qiagen). For transcriptomic analyses, RNA was labeled and hybridized to HG-U133A microarrays (Affymetrix) as previously described[26]. For quantitative RT-PCR studies, complementary DNA was synthesized from 1 µg of total RNA using a reverse transcriptase kit (Applied Biosystems). Gene expression levels were determined using commercially available Taqman gene expression assays for the lung metastasis genes of interest, and beta 2-microglobulin was used as an endogenous control (Applied Biosystems). Real-time expression data were acquired and analyzed using an AB1 Prism 7900HT Sequence Detection System (Applied Biosystems).

Intravasation. To measure metastatic cells in circulation, parental or LM2 cells were infected with pBabe retrovirus expressing a selectable puromicin marker. Infected cells were injected into the mammary fat pad of immunodeficient mice and tumor volumes measured as previously described[12]. Animals bearing palpable tumors were euthanized and bled through cardiac punctures. Approximately 1-2 ml of blood was drawn, lysed for red blood cells using ACK lysis buffer (Cambrex), and the remaining cells were re-plated into DMEM supplemented with 10% FBS, glutamine, penicillin and streptomycin. Following 48 h, adherent cells were grown in media with puromycin to select for tumor cells. After 10 days, tumor colonies recovered from circulation were stained with crystal violet blue and scored under microscopy.

Mammary tumor colonization assays. Both the parental MDA-MB-231 population and its metastatic derivative LM2 cells were infected with retrovirus expressing either a thymidine kinase-GFP-firefly luciferase (TGL) or a thymidine kinase-RFP-renilla luciferase (TRL) fusion protein[27]. Infected cells were sorted by FACS. To assess mammary tumor seeding from circulation, $1 \times 10^6$ RFP expressing parental cells were first implanted into mammary gland #2 of immunodeficient mice as previously described[12]. Once these RFP expressing tumors became palpable (100 mm$^3$), $1 \times 10^5$ GFP-luciferase expressing LM2 or parental cells were injected into the left ventricle of tumor-bearing animals. Colonization of mammary tumors was determined by luciferase bioluminescence measurements. Animals were sacrificed after 36 days, tumors removed, fixed in 4% paraformaldehyde, and frozen in OCT. Confirmation of mammary tumor seeding was achieved by visualizing tumor sections with a Zeiss Axiovert 200M microscope, as well as a Leica TCS SP2 AOBS inverted confocal microscope.

In the cross-seeding experiments, $1 \times 10^6$ of RFP expressing LM2 cells were injected into the left mammary fat pad, while the same amount of GFP expressing LM2 cells implanted into the contra-lateral fat pad. After approximately 8 weeks, tumors were resected, fixed, and frozen in OCT. GFP positive cells cross-seeding into an established RFP tumor were visualized under confocal microscopy.

Example II

Experimental Results—Lung Metastasis Genes Couple Breast Tumor Size and Metastatic Spread; Mammary Tumor Colonization Assays The consistent association of large tumor size, rapid growth rate, and metastatic behavior in a majority of cases of clinical cancer suggests that the molecular bases of these phenomena may be linked[1-4]. However, prior to the present invention, the nature of this link was not well-understood. Some models of metastasis envision rare metastatically competent variants emerging by chance as primary tumors grow, causally linking growth with likelihood of metastatic relapse[5, 6]. Alternative models posit that pro-metastatic gene expression events are acquired early during tumorigenesis, with tumor size being a marker of aggressiveness[7-11]. We previously identified in breast cancer a lung-metastasis gene-expression signature (LMS) comprising genes that not only promote lung metastasis but also foster mammary tumor growth in mice[12]. In a mouse model system, we demonstrate herein that cells expressing the LMS have a selective growth advantage in primary breast tumors, and furthermore, that progressive primary tumor growth enables LMS+ breast cancer cells to gain access to the circulation and not only seed the distant lung but also self-seed the primary tumor. Without wishing to be bound by any particular mechanism, it is suggested that the discernible expression of a pre-existing lung metastasis signature within primary breast tumors is therefore both a cause and a consequence of its ability to mediate primary tumor growth as well as metastatic colonization. This model for the coupling of primary tumor growth and lung metastatic activity by genetic mediators combines elements from both the stochastic progression and early determination models of cancer metastasis.

We previously used the human breast cancer cell line MDA-MB-231 in a mouse xenograft model to select cell subpopulations that are metastatic to lung[12]. These populations share a gene expression signature that is associated with their ability to colonize the lungs. Many of the genes that comprise this signature (e.g. ID1, MMP1, PTGS2/COX29, Epiregulin, CXCL1, IL13RA2 and VCAM1) have been functionally validated as mediators of lung metastasis from the circulation in a mouse model[12]. A subset of these genes, called the "lung metastasis gene-expression signature" (LMS), is expressed in a subgroup of human primary breast tumors with a pattern resembling the canonical expression profile of these genes in the lung metastatic cell lines. The expression of these genes in primary tumors suggested a role in primary tumor growth in addition to their role as mediators of lung colonization from the circulation[12].

If the LMS confers a growth advantage in the primary site besides promoting lung metastasis, then the LMS could provide a functional link between primary tumor size and poor disease outcome.

Figure 1:
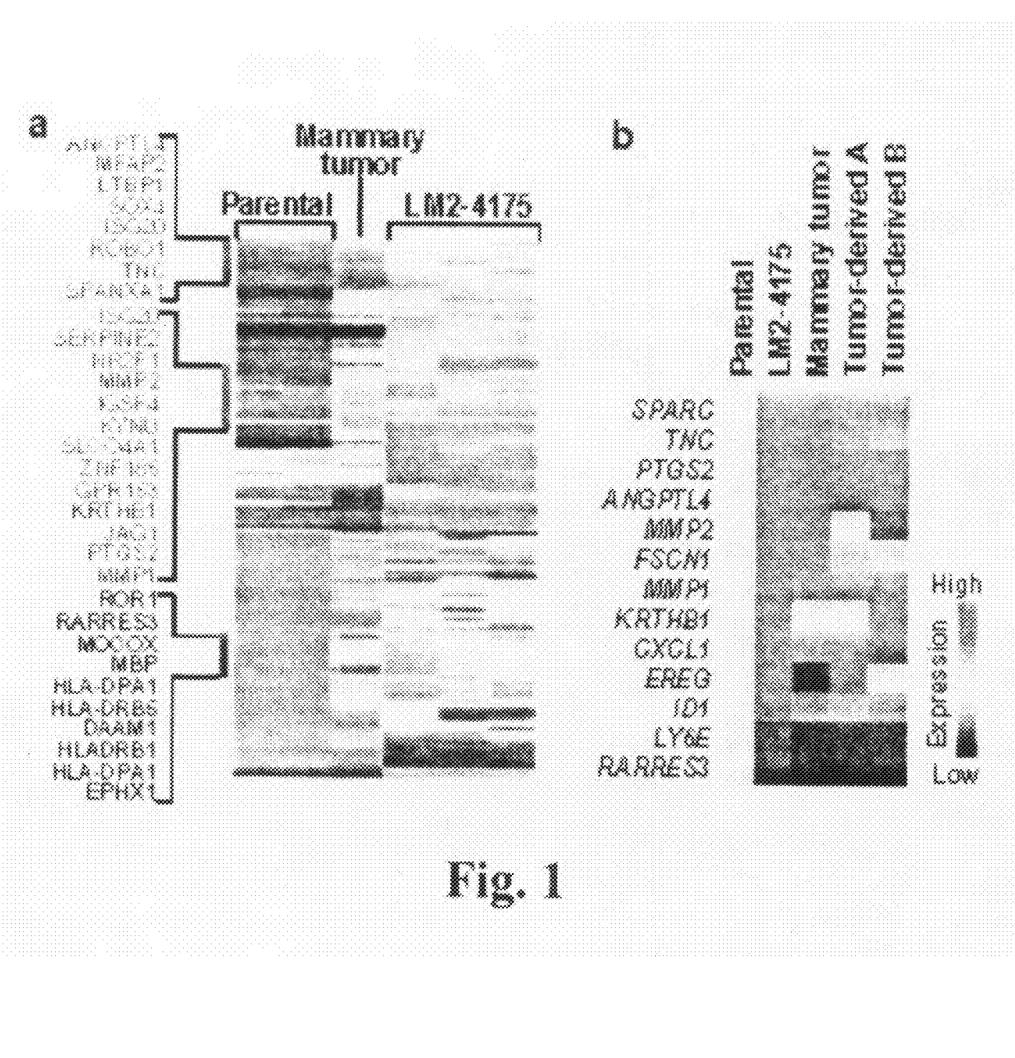
FIG. 1 shows enrichment for the lung metastatic signature (LMS) during mammary tumorigenesis.

To more directly examine the relationship between LMS expression, large tumor size, and distant metastasis, we utilized a xenograft model of breast cancer. In this context, we have previously shown that LMS$^+$ cells drive more rapid tumor growth than do their LMS$^-$ counterparts[12]. This property suggests the possibility that cells expressing the LMS in a primary tumor might have a selective advantage. To test this prediction we established mammary fat pad tumors with the parental MDA-MB-231 cell line, which harbors a small LMS+ subpopulation of lung metastatic cells. Gene expression profiling (FIG. 1a) and quantitative RT-PCR analysis for LMS genes (FIG. 1b) demonstrated a partial enrichment for the expression of LMS genes both in tumors generated from the parental MDA-MB-231 population and in cell cultures derived from these tumors. These observations suggest that LMS+ cells within a breast cancer population have a growth advantage that can be efficiently selected for during primary tumorigenesis and progression.

Figure 2:
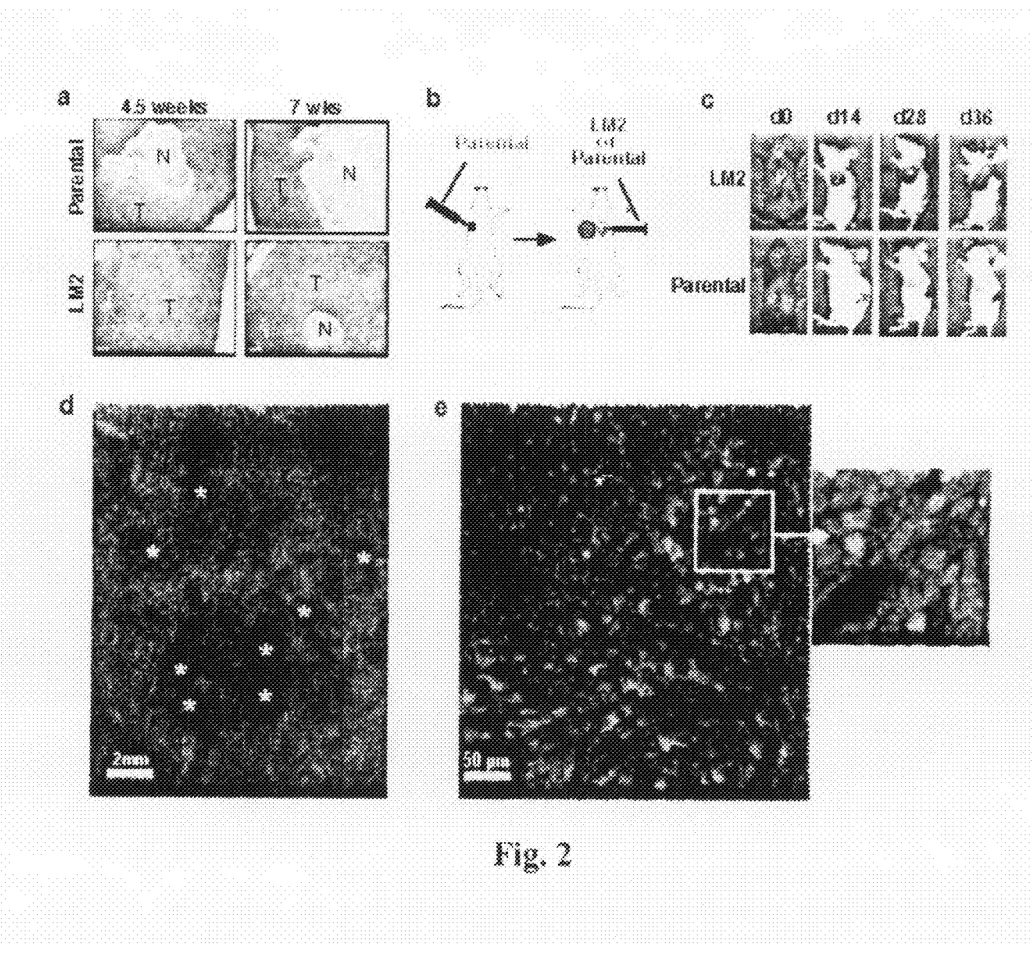
FIG. 2 shows that LMS-positive cells from circulation can colonize a pre-established mammary tumor.
Figure 3:
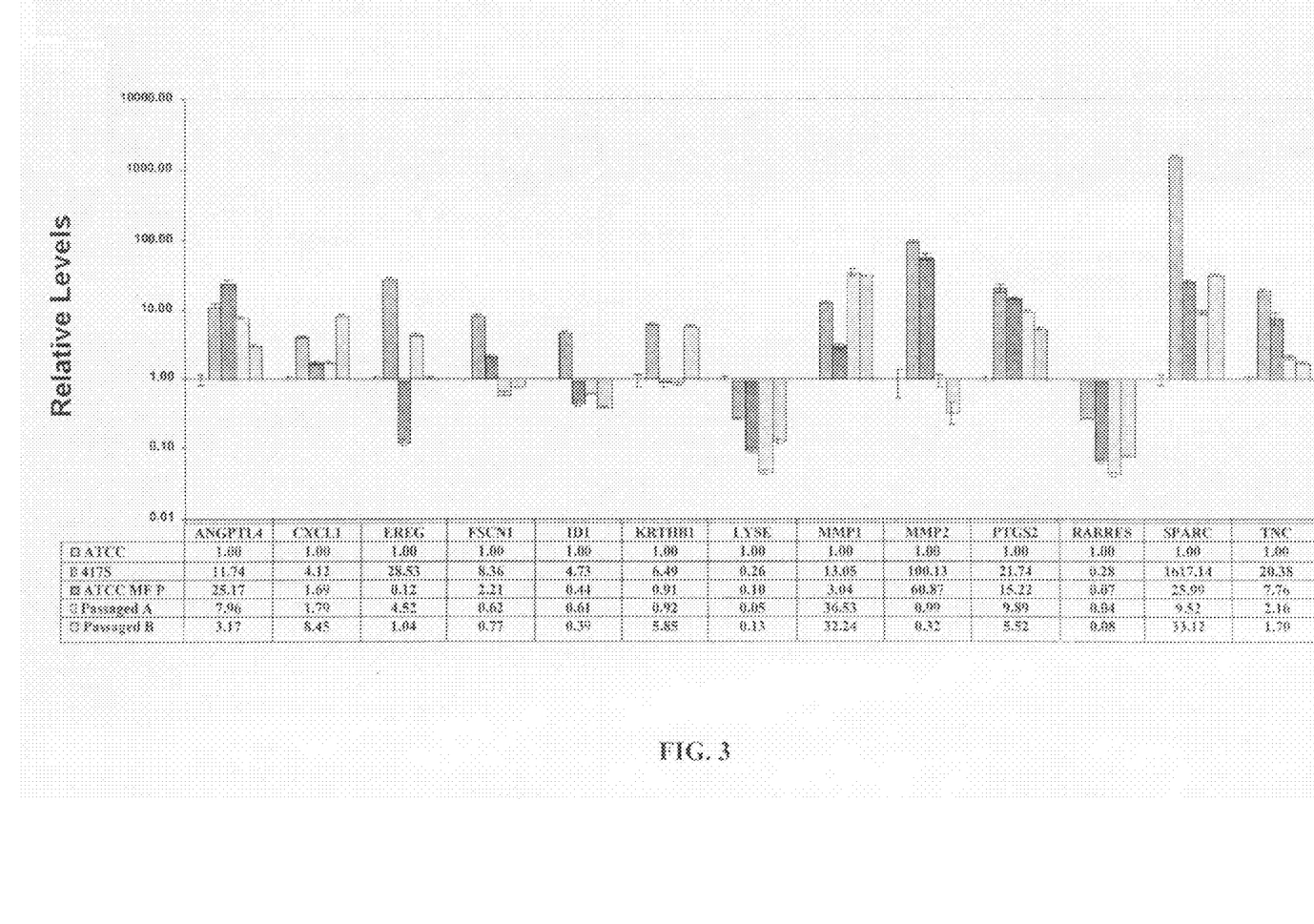
FIG. 3 shows LMS enrichment during growth of parental MDA-MB-231 cells as mammary tumors. Relative levels of expression of LMS genes in parental MDA-MB-231 cells, mammary tumors generated by these cells, two different cell lines derived from these tumors, and the in vivo-selected LMS$^+$ cell lines LM2-4175 mRNA levels for thirteen of the genes in the LMS (11 up-regulated genes and two down-regulated genes) were determined by qRT-PCR. The values (n=3±SD) are tabulated and graphically plotted.

Without wishing to be bound by any particular mechanism, it is suggested that the clinical observation that LMS+ tumors are larger and that larger LMS+ tumors are more likely metastatic may at least partially be explained by experimental data indicating that the activities encoded by the LMS stimulate a direct in situ expansion of the tumor cell subpopulation. Compared to their parental MDA-MB-231 population, LMS$^+$ subpopulations (LM2 cells) selected by in vivo passage through the lungs of immunodeficient mice[12] form faster-growing, less necrotic tumors when implanted in mouse mammary glands (FIG. 2a; ref.[12]). Necrotic regions of primary tumors are non-viable and can correlate with elevated interstitial pressure, resulting from increased cell density and tumor size[16, 17]. Indeed, some of the genes included in the LMS can stimulate tumor angiogenesis (our unpublished work), which promotes tumor growth[18-20]. However, several of the products encoded by the LMS mediate extravasation from lung capillaries and tumor-initiating activity, which are functions more clearly associated with tumorigenic colonization from the circulation rather than with direct in situ expansion of a tumor cell population. We tested whether, besides causing local tumor expansion by in situ growth, the colonizing functions provided by the LMS participate not only in metastatic spread to the lungs but also in a circulation-based "self-seeding" of primary tumors[21]. Tumor growth and metastatic potential would thereby have a common mechanistic link.

To determine whether circulating LMS$^+$ breast cancer cells can colonize a pre-established primary tumor, parental MDA-MB-231 cells expressing red fluorescent protein (RFP) were implanted into the mouse mammary fat pad. Once these tumors became palpable (around 100 mm$^3$), either parental or LM2 cells engineered to stably express firefly luciferase and green fluorescent protein (GFP) were injected intracardially into the arterial circulation of these tumor-bearing mice (FIG. 2b). This ensured a distribution of circulating tumor cells throughout the animal (FIG. 2c, day 0). Notably, the bioluminescent signal emitted by inoculated LM2 cells was initially retained and subsequently intensified over time in the pre-established mammary tumors, suggesting expansion of the luciferase-positive cell population (FIG. 2c, days 14-36). This was confirmed by immunofluorescence microscopy, demonstrating the ability of GFP-positive LM2 cells to colonize and outgrow amidst the RFP-positive parental cells of the primary tumor (FIGS. 2d, e). Colonization by LM2 cells was prevalent particularly within the necrotic core (FIG. 2d), indicating an ability to colonize where parental cells succumb. No colonization occurred in tumor-free mammary glands (FIG. 2c), consistent with the fact that LM2 cells do not spontaneously generate new primary tumors from circulation even though they avidly colonize the lungs[12]. Remarkably, parental cells were unable to colonize a pre-established tumor (FIG. 2c, and immunofluorescence data not shown). Consequently, a developing primary tumor can attract and be colonized by tumor cells in the circulation, and the colonizing ability of these cells is dependent on the LMS.

We also tested whether the colonizing activity conferred by the LMS could be exerted when the source of circulating LMS+ cells is an endogenous tumor. LM2 cells growing as mammary tumors initially do not intravasate into the circulation; however, progressive growth of the primary tumor leads to the ability to readily move into the circulation (FIG. 2f). Once in the circulation, as few as several hundred cells are needed to form lung metastases (ref[12] and data not shown). However, the return of these cells to seed the source tumor would be expected to encounter an unfavorable circulatory pattern with lung capillary beds that retain circulating tumor cells. To determine if cells released from a tumor in the mammary gland can return to a tumor growing at that site in spite of these barriers, we implanted RFP-labeled LM2 cells into one mammary fat pad, and GFP-expressing LM2 cells into a contra-lateral fat pad (FIG. 2g). As a control, mice were implanted with RFP-expressing LM2 cells only. Numerous lung metastases developed under these conditions (data not shown), as previously described[12]. Despite this capture within the lungs, fluorescence microscopy detected numerous cells from one fluorescently labeled LM2 tumor that had colonized the contra-lateral LM2 tumor expressing the other marker (FIG. 2h). This cross-seeding of circulating cancer cells presumably also reflects self-seeding of the original tumor, although this could not be directly visualized because the fluorescent marker in the implanted and the seeded cells would be the same. No seeding of tumor cells to intact mammary fat pads was observed (data not shown). Collectively, these results suggest that progressive growth results in expansion of LM2 cells within the primary tumor and a subsequent gain in the ability to invade the circulation, where they can not only metastasize to the lungs but also self-seed the primary site.

Whether through in situ expansion or through the colonizing capacity provided by the LMS, our data are consistent with the proposal that the LMS confers a selective advantage for primary tumor cells to thrive where their growth would be otherwise restricted. The data suggest that, without the need for additional genetic alterations, the functions encoded by the LMS can drive the expansion of a pool of metastatically competent cells for continuous selection at the primary site. The significance of self-seeding as a possible mechanism that contributes to primary tumor growth is based on mathematical considerations whereby continuous self-seeding of a primary tumor by its own aggressive cells would accelerate tumor growth[21]. Without wishing to be bound by any particular mechanism, it is suggested that the consequent linkage between metastasis-promoting gene expression, accelerated tumor growth, and the likelihood of metastatic recurrence may help to explain the repeated observation of prognostic gene expression signatures in primary malignancies[7-9, 11, 13, 14, 22].

Tumor size is frequently identified as an independent variable associated with metastasis in clinical studies[2-4] and studies on poor-prognosis gene-expression signatures[8, 9, 23]. However, it has been unclear whether tumor growth leads to metastasis or whether aggressive growth is a marker for cells destined to metastasize. Here, we show both can be true. Our data suggest that tumor growth can lead to the expansion of LMS+ cells in the primary tumor. Further growth is then associated with LMS+ cells entering the circulation where they can seed distant sites or re-seed the primary tumor. Subsequently, continued primary tumor growth is a marker for metastasis because the colonizing ability of LMS+ cells concomitantly contributes to their expansion at the primary site as well as to their growth in the lungs. Our clinical and experimental data suggest that this transition may be associated with a threshold tumor size. The LMS group of genes includes validated mediators of lung metastasis from the circulation that also confer aggressive tumor growth at the primary site[12].

Example III

An in Vitro Assay System

Putative anti metastatic and anticancer compounds are screened in an in vitro system. Tumorigenic (and/or metastatic) cells labeled with a first detectable label are allowed to form colonies in a soft agar growth system, using any of a variety of well-known methods. For example: a layer is prepared of 0.6% agar in Dulbecco's Modified Eagle Medium (DMEM), which is allowed to set (to solidify) in a suitable culture dish. Cells containing the first detectable label are harvested and manipulated to create a single cell suspension having a suitable cell count. These cells are resuspended in an 0.3% agar solution in DMEM and distributed onto the base agar layer. Once the cells-agar mix has solidified, it is overlayed with a suitable tissue culture medium. The cells are fed under conventional conditions (e.g. every 5 days) with a suitable tissue culture medium. The cells are incubated until colonies form (e.g. for about 7-15 days at 37° C.). After colonies are observed, the tissue culture medium is removed and overlayed with a 0.3% agar solution in DMEM containing a single cell suspension of metastatic cells that are labeled with a second detectable label. The cells are then overlayed with a suitable tissue culture media containing the compound to be tested or screened. The metastatic cells containing the second label are allowed to form colonies. The number, position and size of colonies containing each of the labels is determined by direct visual analysis or by automatic confocal microscopy, and the degree of coating/infiltration of each labeled colony by cells containing the other label is determined. The cells can be grown in multi-well plates, for example 96-well plates, and the method can be adapted for high-throughput screening.

Example IV

Assay for Agents that Inhibit Metastatic Cells

Putative agents are tested for their ability to inhibit a metastatic cell, using an assay of the invention. In one assay, using methods as described elsewhere herein, detectably labeled metastatic cells are inoculated into immunodeficient mice bearing tumors, and the mice are then treated with agents that belong to the Epiregulin class of growth factors (also known as EREG, a ligand of the EGFR/HER receptor family). Among the agents tested are agents that target the EGF receptor (including Erbitux, Iressa and Tarceva) and agents that target HER2 (e.g., Herceptin). It is expected that these agents will inhibit the seeding of the metastatic cells in the assay to a similar degree to which they inhibit metastasis. For example, preliminary results suggest that Erbitux but not Herceptin inhibits lung metastasis as a single agent; a similar result is found with the seeding assay of the invention. Other agents that are tested include combinations of HER1/EGFR and/or HER2 inhibitors with Celecoxib (Pfizer), which is a cyclooxygenase synthase-2 (COX-2) inhibitor. Another agent that is tested is Avastin (an anti-VEGF inhibitor that is known to inhibit metastatic tumors), alone or in combination with other agents as above. The action of the agents or combinations of agents in the seeding assay of the invention is expected to mirror the antimetastatic properties of the agents or combinations of agents.

REFERENCES

1. Hellman, S. Karnofsky Memorial Lecture. Natural history of small breast cancers. J Clin Oncol 12, 2229-34 (1994).
2. Koscielny, S. et al. Breast cancer: relationship between the size of the primary tumour and the probability of metastatic dissemination. Br J Cancer 49, 709-15 (1984).
3. Giordano, S. H. et al. Is breast cancer survival improving? Cancer 100, 44-52 (2004).
4. Heimann, R. & Hellman, S. Clinical progression of breast cancer malignant behavior: what to expect and when to expect it. J Clin Oncol 18, 591-9 (2000).
5. Chambers, A. F., Groom, A. C. & MacDonald, I. C. Dissemination and growth of cancer cells in metastatic sites. Nat Rev Cancer 2, 563-72 (2002).
6. Fidler, I. J. The pathogenesis of cancer metastasis: the 'seed and soil' hypothesis revisited. Nat Rev Cancer 3, 453-8 (2003).
7. Ramaswamy, S., Ross, K. N., Lander, E. S. & Golub, T. R. A molecular signature of metastasis in primary solid tumors. Nat Genet 33, 49-54 (2003).
8. van't Veer, L. J. et al. Gene expression profiling predicts clinical outcome of breast cancer. Nature 415, 530-6 (2002).
9. van de Vijver, M. J. et al. A gene-expression signature as a predictor of survival in breast cancer. N Engl J Med 347, 1999-2009 (2002).
10. Bernards, R. & Weinberg, R. A. A progression puzzle. Nature 418, 823 (2002).
11. Wang, Y. et al. Gene-expression profiles to predict distant metastasis of lymph-node-negative primary breast cancer. Lancet 365, 671-9 (2005).
12. Minn, A. J. et al. Genes that mediate breast cancer metastasis to lung. Nature 436, 518-24 (2005).

13. Smid, M. et al. Genes associated with breast cancer metastatic to bone. J Clin Oncol 24, 2261-7 (2006).
14. Sorlie, T. et al. Repeated observation of breast tumor subtypes in independent gene expression data sets. Proc Natl Acad Sci USA 100, 8418-23 (2003).
15. Tusher, V. G., Tibshirani, R. & Chu, G. Significance analysis of microarrays applied to the ionizing radiation response. Proc Natl Acad Sci USA 98, 5116-21 (2001).
16. Heldin, C. H., Rubin, K., Pietras, K. & Ostman, A. High interstitial fluid pressure—an obstacle in cancer therapy. Nat Rev Cancer 4, 806-13 (2004).
17. Padera, T. P. et al. Pathology: cancer cells compress intratumour vessels. Nature 427, 695 (2004).
18. Carmeliet, P. Angiogenesis in life, disease and medicine. Nature 438, 932-6 (2005).
19. Ferrara, N. & Kerbel, R. S. Angiogenesis as a therapeutic target. Nature 438, 967-74 (2005).
20. Folkman, J. Role of angiogenesis in tumor growth and metastasis. Semin Oncol 29, 15-8 (2002).
21. Norton, L. & Massagué, J. Is cancer a disease of self-seeding? Nat Med Submitted for publication (2006).
22. Chang, H. Y. et al. Robustness, scalability, and integration of a wound-response gene expression signature in predicting breast cancer survival. Proc Natl Acad Sci USA 102, 3738-43 (2005).
23. Hu, Z. et al. The molecular portraits of breast tumors are conserved across microarray platforms. BMC Genomics 7, 96 (2006).
24. Minn, A. J. et al. Genes that mediate breast cancer metastasis to lung. Nature in press (2005).
25. Saeed, A. I. et al. TM4: a free, open-source system for microarray data management and analysis. Biotechniques 34, 374-8 (2003).
26. Kang, Y. et al. A multigenic program mediating breast cancer metastasis to bone. Cancer Cell 3, 537-49 (2003).
27. Ponomarev, V. et al. A novel triple-modality reporter gene for whole-body fluorescent, bioluminescent, and nuclear noninvasive imaging. Eur J Nucl Med Mol Imaging 31, 740-51 (2004).

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding specific embodiments are to be construed as merely illustrative, and not limiting of the scope of the invention in any way whatsoever. The entire disclosure of all applications, patents and publications (including reference manuals) cited above and in the figures, are hereby incorporated in their entirety by reference.

We claim:

1. A method for identifying an agent that inhibits a metastatic cell, comprising,
measuring the amount of seeding of a pre-existing tumor by a detectably labeled, metastatic cell, in a subject, in the presence and absence of a putative agent,
wherein the amount of seeding by the metastatic cell is proportional to the metastatic potential of the cell, and
wherein a significant amount of inhibition of the seeding by the putative agent indicates that the putative agent is effective to inhibit the metastatic cell.

2. The method of claim 1, wherein the amount of seeding by the metastatic cell is determined by measuring the amount of the detectable label at the site of the tumor.

3. The method of claim 1, wherein the detectable label is a fluorescent marker or luciferase.

4. The method of claim 3, wherein the label is detected by, when the metastatic cell is labeled with a fluorescent marker, examining, with a fluorescent microscope, a tissue sample from the tumor of the subject, or
when the metastatic cell is labeled with luciferase, examining the tumor in the living subject by measuring light emission from the marker.

5. The method of claim 1, comprising
introducing a cell from a tumor or tumorigenic cell line into a suitable site of an immuno-compromised subject and allowing the cell to form a tumor,
introducing into the subject, by a systemic route, a detectably labeled metastatic cell from a cell line that has been derived from the tumor or tumorigenic line, and
measuring the amount of seeding of the tumor by the metastatic cell in the presence and absence of the agent.

6. The method of claim 5, wherein the tumorigenic cell is from a breast tumor or a tumorigenic cell line derived from a breast tumor; and the metastatic cell is a derivative of the tumorigenic cell which metastasizes preferentially to lung, bone or brain.

7. The method of claim 6, wherein the metastatic cell metastasizes preferentially to lung.

8. . The method of claim 7, wherein the tumor is grown from an MDA-MB-231 cell; and the metastatic cell is an LM2 cell, which is metastatic derivative of the MDA-MB-231 cell.

9. The method of claim 1, comprising
allowing a tumor to form in a cancer-prone subject,
introducing into the subject having the tumor, by a systemic route, a detectably labeled metastatic cell, and
measuring the amount of seeding of the tumor by the metastatic cell in the presence and absence of the agent.

10. The method of claim 1, wherein the seeding that is measured is the seeding by a cell from a first tumor grown from a cell from metastatic cell line, to a second tumor grown from another cell from the metastatic cell line.

11. The method of claim 10, comprising,
introducing a first detectably labeled cell from a metastatic cell line into a first suitable site of an immuno-compromised subject,
introducing a second cell from the metastatic cell line into a second suitable site of the subject,
allowing the first and second cells to form tumors, and
measuring, in the presence and absence of the putative agent, the amount of seeding of labeled cells from the tumor at the first site to the tumor at the second site.

12. The method of claim 11, further wherein the second cell from the metastatic cell line is labeled with a second detectable label, which can be distinguished from the first detectable label, and the amount of seeding of labeled cells shed from the tumor at the second site to the tumor at the tumor at the first site is also measured, in the presence and absence of the putative agent.

13. The method of claim 1, wherein a plurality of the following genes listed in Table 1 are significantly up-regulated or down-regulated in the metastatic cell: FSCN1, MMP1, ANGPTL4, C10orf116, CXCL1, PTGS2/COX2, KRTHB1, VCAM1, RARRES3, LTBP1, KYNU, CXCR4, LY6E, ID1, MAN1A1, NEDD9, EREG (epiregulin), TNC.

14. The method of claim 1, wherein two or more of the following genes are up-regulated in the metastatic cell: MMP1, CXCL1, PTGS2/COX2, VCAM1, ID1, epiregulin, MMP2, SPARC, IL13R2, TNC, FSCN1, ANGPTL4, or CXCL1.

15. The method of claim 1, wherein the following genes are up-regulated in the metastatic cell:

epiregulin in combination with one or more of MMP 1, MMP2 or PTGS2;
MMP 1, MMP2 and PTGS2;
one or more of TNC, FSCN1, ANGPTL4 or CXCL1;
TNC and FSCN1;
TNC and ANGPTL4; or
ANGPTL4 and KRTHB 1.

16. The method of claim 1, wherein the metastatic cell is obtained by serially passaging metastasized cells from a tumor or tumorigenic cell line though immuno-compromised animals, to obtain cells in each round of passage cells that are more metastatic than the cells from the previous round of passage.

17. The method of claim 1, wherein the metastatic cell is generated by transfecting a suitable host cell with one or more of the following up-regulated genes listed in Table 1: FSCN1, MMP1, ANGPTL4, C10orf116, CXCL1, PTGS2/COX2, KRTHB1, VCAM1, LTBP1, KYNU, ID1, MAN1A1, EREG (epiregulin), TNC.

18. The method of claim 1, wherein the metastatic cell is generated by transfecting a suitable host cell with one or more of the following genes: MMP1, CXCL1, PTGS2/COX2, VCAM1, ID1, epiregulin, MMP2, SPARC, IL13R2, TNC, FSCN1, ANGPTL4, or CXCL1.

19. The method of claim 1, wherein the metastatic cell is generated by transfecting a suitable host cell with one or more of the following genes:
epiregulin in combination with one or more of MMP 1, MMP2 or PTGS2;
MMP 1, MMP2 and PTGS2;
one or more of TNC, FSCN1, ANGPTL4 or CXCL1;
TNC and FSCN1;
TNC and ANGPTL4; or
ANGPTL4 and KRTHB 1.

20. The method of claim 1, which is a method for identifying an agent for treating a subject having a tumor.

* * * * *